United States Patent
Eitan et al.

(10) Patent No.: US 12,011,567 B2
(45) Date of Patent: Jun. 18, 2024

(54) FLEX-STROKE INFUSION PUMP

(71) Applicant: EITAN MEDICAL LTD., Netanya (IL)

(72) Inventors: Boaz Eitan, Hofit (IL); Ram Shtoltz, Tel-Aviv (IL); Amir Rasowsky, Yakir (IL); Gidi Pesach, Kfar Vitkin (IL); Nir Ovadia, Netanya (IL)

(73) Assignee: EITAN MEDICAL LTD., Netanya (IL)

( * ) Notice: Subject to any disclaimer, the term of this patent is extended or adjusted under 35 U.S.C. 154(b) by 982 days.

(21) Appl. No.: 16/967,952

(22) PCT Filed: Apr. 9, 2018

(86) PCT No.: PCT/IL2018/050409
§ 371 (c)(1),
(2) Date: Aug. 6, 2020

(87) PCT Pub. No.: WO2019/155453
PCT Pub. Date: Aug. 15, 2019

(65) Prior Publication Data
US 2021/0001036 A1    Jan. 7, 2021

Related U.S. Application Data

(60) Provisional application No. 62/629,038, filed on Feb. 11, 2018.

(51) Int. Cl.
*A61M 5/145* (2006.01)
*A61M 5/142* (2006.01)
*A61M 5/168* (2006.01)

(52) U.S. Cl.
CPC ...... *A61M 5/1452* (2013.01); *A61M 5/16881* (2013.01); *A61M 2005/14208* (2013.01); *A61M 2205/02* (2013.01)

(58) Field of Classification Search
CPC ............ A61M 5/1452; A61M 5/16881; A61M 2005/14208; A61M 2205/02; A61M 5/14216; A61M 5/16813; F04B 43/08
See application file for complete search history.

(56) References Cited

U.S. PATENT DOCUMENTS

| | | | |
|---|---|---|---|
| 3,379,950 A | 4/1968 | Friedline | |
| 3,778,195 A | 12/1973 | Bamberg | |

(Continued)

FOREIGN PATENT DOCUMENTS

| | | | |
|---|---|---|---|
| EP | 0182502 A2 | 5/1986 | |
| EP | 1381843 | 3/2009 | |

(Continued)

OTHER PUBLICATIONS

Extended European Search Report for European Application No. 21194042.4, dated Feb. 17, 2022., 7 pp.

(Continued)

*Primary Examiner* — Theodore J Stigell
(74) *Attorney, Agent, or Firm* — The Roy Gross Law Firm, LLC; Roy Gross

(57) ABSTRACT

An infusion pump including a plunger, a proximal valve located proximally to the plunger, a distal valve located distally to the plunger, and a controller configured to trigger the position of the plunger, such that both in its upper position and its lower position, the plunger squeezes a section of an infusion tube, such that opposite sides of an inner surface of the section do not contact one another.

19 Claims, 5 Drawing Sheets

(56) References Cited

U.S. PATENT DOCUMENTS

| | | |
|---|---|---|
| 4,236,880 A | 12/1980 | Archibald |
| 4,314,567 A * | 2/1982 | Cannon ............. A61M 5/16813 128/DIG. 13 |
| 4,322,668 A | 3/1982 | Trussler et al. |
| 4,391,600 A | 7/1983 | Archibald |
| 4,650,469 A | 3/1987 | Berg et al. |
| 5,018,945 A | 5/1991 | D'Silva |
| 5,049,047 A | 9/1991 | Polaschegg et al. |
| 5,096,385 A | 3/1992 | Georgi et al. |
| 5,116,203 A * | 5/1992 | Natwick ............ A61M 5/16854 417/474 |
| 5,340,951 A | 8/1994 | Hungerbuhler et al. |
| 5,437,642 A | 8/1995 | Thill et al. |
| 5,807,075 A | 9/1998 | Jacobsen et al. |
| 5,807,322 A | 9/1998 | Lindsey et al. |
| 5,843,035 A | 12/1998 | Bowman et al. |
| 5,924,852 A | 7/1999 | Moubayed et al. |
| 5,954,485 A | 9/1999 | Johnson et al. |
| 6,312,227 B1 | 11/2001 | Davis |
| 6,494,864 B1 | 12/2002 | Kerwin et al. |
| 6,523,414 B1 | 2/2003 | Malmstrom et al. |
| 6,531,708 B1 | 3/2003 | Malmstrom et al. |
| 6,554,806 B2 | 4/2003 | Butterfield et al. |
| 6,659,976 B2 | 12/2003 | Beck et al. |
| 6,679,862 B2 | 1/2004 | Diaz et al. |
| 6,702,779 B2 | 3/2004 | Connelly et al. |
| 6,750,468 B2 | 6/2004 | Malmstrom et al. |
| 6,852,094 B2 | 2/2005 | Beck et al. |
| 6,889,556 B2 | 5/2005 | Steger |
| 6,907,788 B2 | 6/2005 | Malmstrom et al. |
| 6,908,452 B2 | 6/2005 | Diaz et al. |
| 6,979,311 B2 | 12/2005 | Miles et al. |
| 7,048,715 B2 | 5/2006 | Diaz et al. |
| 7,059,840 B2 | 6/2006 | Corwin et al. |
| 7,070,575 B2 | 7/2006 | Beck et al. |
| 7,092,796 B2 | 8/2006 | Vanderveen |
| 7,121,143 B2 | 10/2006 | Malmstrom et al. |
| 7,163,381 B1 | 1/2007 | Barak |
| 7,356,382 B2 | 4/2008 | Vanderveen |
| 7,384,408 B2 | 6/2008 | Barak |
| 7,497,842 B2 | 3/2009 | Diaz et al. |
| 7,695,448 B2 | 4/2010 | Cassidy et al. |
| 7,726,174 B2 | 6/2010 | Riley et al. |
| 7,758,551 B2 | 7/2010 | Wiesner et al. |
| 7,819,838 B2 | 10/2010 | Ziegler et al. |
| 7,875,004 B2 | 1/2011 | Yodfat et al. |
| 7,881,883 B2 | 2/2011 | Remde |
| 7,892,199 B2 | 2/2011 | Mhatre et al. |
| 7,896,197 B2 | 3/2011 | Furey et al. |
| 7,921,718 B2 | 4/2011 | Malmstrom et al. |
| 7,922,700 B2 | 4/2011 | Evans et al. |
| 7,967,773 B2 | 6/2011 | Amborn et al. |
| 7,981,082 B2 | 7/2011 | Wang et al. |
| 8,025,654 B2 | 9/2011 | Barak |
| 8,034,020 B2 | 10/2011 | Dewey |
| 8,048,022 B2 | 11/2011 | Moy et al. |
| 8,081,069 B2 | 12/2011 | Haueter et al. |
| 8,105,269 B2 | 1/2012 | Zhou |
| 8,142,400 B2 | 3/2012 | Rotem et al. |
| 8,152,780 B2 | 4/2012 | Evans et al. |
| 8,167,832 B2 | 5/2012 | Bowman et al. |
| 8,182,461 B2 | 5/2012 | Pope et al. |
| 8,225,639 B2 | 7/2012 | Riley et al. |
| 8,232,484 B2 | 7/2012 | Hauck |
| 8,286,505 B2 | 10/2012 | Wade |
| 8,287,495 B2 | 10/2012 | Michaud et al. |
| 8,298,184 B2 | 10/2012 | Diperna et al. |
| 8,328,786 B2 | 12/2012 | Strickler et al. |
| 8,343,111 B2 | 1/2013 | Beck et al. |
| 8,361,021 B2 | 1/2013 | Wang et al. |
| 8,378,837 B2 | 2/2013 | Wang et al. |
| 8,394,051 B2 | 3/2013 | Geipel |
| 8,419,676 B2 | 4/2013 | Evans et al. |
| 8,448,523 B2 | 5/2013 | Richter |
| 8,486,005 B2 | 7/2013 | Yodfat et al. |
| 8,486,020 B2 | 7/2013 | Hills et al. |
| 8,496,613 B2 | 7/2013 | Zhou |
| 8,539,672 B2 | 9/2013 | Eggers et al. |
| 8,567,235 B2 | 10/2013 | Bojan et al. |
| 8,641,671 B2 | 2/2014 | Michaud et al. |
| 8,657,778 B2 | 2/2014 | Ziegler et al. |
| 8,690,014 B2 | 4/2014 | Haueter et al. |
| 8,690,860 B2 | 4/2014 | Abal |
| 8,733,178 B2 | 5/2014 | Bivans et al. |
| 8,752,436 B2 | 6/2014 | Beck et al. |
| 8,758,323 B2 | 6/2014 | Michaud et al. |
| 8,771,227 B2 | 7/2014 | Connelly et al. |
| 8,795,225 B2 | 8/2014 | Lewis et al. |
| 8,808,230 B2 | 8/2014 | Rotstein |
| 8,821,432 B2 | 9/2014 | Unverdorben |
| 8,852,141 B2 | 10/2014 | Mhatre et al. |
| 8,859,972 B2 | 10/2014 | Cummings et al. |
| 8,876,787 B2 | 11/2014 | Beck et al. |
| 8,900,213 B2 | 12/2014 | Pope et al. |
| 8,926,561 B2 | 1/2015 | Verhoef et al. |
| 8,943,894 B2 | 2/2015 | Geipel |
| 8,945,064 B2 | 2/2015 | Gravesen et al. |
| 8,961,453 B2 | 2/2015 | Bowman et al. |
| 8,974,415 B2 | 3/2015 | Robert et al. |
| 8,986,253 B2 | 3/2015 | Diperna et al. |
| 9,004,886 B2 | 4/2015 | Beck et al. |
| 9,005,153 B2 | 4/2015 | Kopperschmidt et al. |
| 9,017,296 B2 | 4/2015 | Beck et al. |
| 9,033,923 B2 | 5/2015 | Hartman et al. |
| 9,101,712 B2 | 8/2015 | Denis et al. |
| 9,109,966 B2 | 8/2015 | Duits |
| 9,132,230 B2 | 9/2015 | Blomquist |
| 9,162,023 B2 | 10/2015 | Barnes et al. |
| 9,173,998 B2 | 11/2015 | Rosinko et al. |
| 9,211,377 B2 | 12/2015 | Diperna et al. |
| 9,227,008 B2 | 1/2016 | Magnenat et al. |
| 9,234,850 B2 | 1/2016 | Hammond et al. |
| 9,248,230 B2 | 2/2016 | Geipel et al. |
| 9,272,087 B2 | 3/2016 | Halbert et al. |
| 9,285,324 B2 | 3/2016 | Leuenberger Jockel |
| 9,308,323 B2 | 4/2016 | Adams |
| 9,375,531 B1 | 6/2016 | Lee et al. |
| 9,408,968 B2 | 8/2016 | Browne et al. |
| 9,415,158 B2 | 8/2016 | Miller et al. |
| 9,427,521 B2 | 8/2016 | Pope et al. |
| 9,468,713 B2 | 10/2016 | Hoenninger, III et al. |
| 9,474,854 B2 | 10/2016 | Mhatre et al. |
| 9,480,793 B2 | 11/2016 | Mhatre et al. |
| 9,480,794 B2 | 11/2016 | Keith et al. |
| 9,545,478 B2 | 1/2017 | Abal |
| 9,561,323 B2 | 2/2017 | Plahey et al. |
| 9,603,998 B2 | 3/2017 | Geipel et al. |
| 9,610,404 B2 | 4/2017 | Rotstein |
| 9,642,777 B2 | 5/2017 | Lewis et al. |
| 9,662,437 B2 | 5/2017 | Moosai |
| 9,675,756 B2 | 6/2017 | Kamen et al. |
| 9,677,555 B2 | 6/2017 | Kamen et al. |
| 9,682,192 B2 | 6/2017 | Marsh et al. |
| 9,683,562 B2 | 6/2017 | Davis et al. |
| 9,717,849 B2 | 8/2017 | Mhatre et al. |
| 9,757,517 B2 | 9/2017 | Eberhard |
| 9,770,552 B2 | 9/2017 | Hartman et al. |
| 9,775,947 B2 | 10/2017 | Keith et al. |
| 9,789,251 B2 | 10/2017 | Robert et al. |
| 9,839,744 B2 | 12/2017 | Muto et al. |
| 9,879,668 B2 | 1/2018 | Yavorsky et al. |
| 9,901,676 B2 | 2/2018 | Mijers et al. |
| 9,932,977 B2 | 4/2018 | Bresina et al. |
| 9,937,290 B2 | 4/2018 | Connelly et al. |
| 9,937,291 B2 | 4/2018 | Eberhard |
| 9,958,344 B2 | 5/2018 | Burkhard |
| 9,962,486 B2 | 5/2018 | Rosinko et al. |
| 9,987,424 B2 | 6/2018 | Kim |
| 9,995,642 B2 | 6/2018 | Shimoyama et al. |
| 10,004,847 B2 | 6/2018 | Wander et al. |
| 10,006,453 B2 | 6/2018 | Girard et al. |
| 10,022,494 B2 | 7/2018 | Shimizu |
| 10,022,495 B2 | 7/2018 | Halbert et al. |
| 10,022,496 B2 | 7/2018 | Geipel et al. |

(56) References Cited

U.S. PATENT DOCUMENTS

| | | |
|---|---|---|
| 10,046,112 B2 | 8/2018 | Oruklu et al. |
| 10,080,836 B2 | 9/2018 | Juretich et al. |
| 10,092,697 B2 | 10/2018 | Nessel et al. |
| 10,112,009 B2 | 10/2018 | Dudar et al. |
| 10,151,646 B2 | 12/2018 | Heo et al. |
| 10,539,453 B2 | 1/2020 | Hauck |
| 2003/0141468 A1 | 7/2003 | Malmstrom et al. |
| 2005/0107923 A1 | 5/2005 | Vanderveen |
| 2006/0173412 A1 | 8/2006 | Susi |
| 2006/0189926 A1 | 8/2006 | Hall et al. |
| 2006/0206054 A1 | 9/2006 | Shekalim |
| 2006/0229531 A1* | 10/2006 | Goldberger ............ A61B 5/153 600/584 |
| 2007/0123781 A1 | 5/2007 | Callahan et al. |
| 2007/0179435 A1 | 8/2007 | Braig et al. |
| 2008/0283296 A1 | 11/2008 | Zamora et al. |
| 2009/0221964 A1 | 9/2009 | Rotem et al. |
| 2009/0240201 A1 | 9/2009 | Rotem et al. |
| 2009/0293588 A1 | 12/2009 | Riley et al. |
| 2010/0106082 A1 | 4/2010 | Zhou |
| 2010/0114001 A1 | 5/2010 | O'Mahony |
| 2010/0212407 A1 | 8/2010 | Stringham et al. |
| 2010/0280446 A1 | 11/2010 | Kalpin |
| 2011/0087165 A1 | 4/2011 | Amborn et al. |
| 2011/0152772 A1 | 6/2011 | Rotem et al. |
| 2011/0190606 A1 | 8/2011 | Gable et al. |
| 2012/0205312 A1 | 8/2012 | Hogard |
| 2012/0238949 A1 | 9/2012 | Kalpin |
| 2012/0330574 A1 | 12/2012 | Ruiter et al. |
| 2013/0035659 A1 | 2/2013 | Hungerford et al. |
| 2013/0071271 A1 | 3/2013 | Rosen et al. |
| 2013/0226129 A1 | 8/2013 | Unverdorben |
| 2013/0336814 A1 | 12/2013 | Kamen et al. |
| 2014/0066850 A1 | 3/2014 | Robert et al. |
| 2014/0119954 A1 | 5/2014 | Schweitzer et al. |
| 2014/0121639 A1 | 5/2014 | Lowery et al. |
| 2014/0228755 A1 | 8/2014 | Darrah et al. |
| 2015/0005732 A1 | 1/2015 | Halbert et al. |
| 2015/0238689 A1 | 8/2015 | Shimizu |
| 2015/0292500 A1 | 10/2015 | Girard et al. |
| 2015/0367120 A1 | 12/2015 | Kusters et al. |
| 2018/0140770 A1 | 5/2018 | Hetchler et al. |
| 2018/0200456 A1 | 7/2018 | Eitan et al. |
| 2018/0318505 A1 | 11/2018 | Eitan et al. |
| 2020/0282138 A1 | 9/2020 | Eitan et al. |

FOREIGN PATENT DOCUMENTS

| | | |
|---|---|---|
| EP | 2040056 | 9/2010 |
| EP | 1381889 | 3/2016 |
| EP | 2570826 | 8/2016 |
| EP | 3705148 A1 | 9/2020 |
| FR | 2553151 A1 | 4/1985 |
| GB | 2150644 A | 7/1985 |
| IN | 103727021 A | 4/2014 |
| WO | 02/068018 | 9/2002 |
| WO | 2012/126744 A1 | 9/2012 |
| WO | 2019/155453 A1 | 8/2019 |
| WO | 2020/178824 A1 | 9/2020 |

OTHER PUBLICATIONS

An Office Action dated Sep. 30, 2019, which issued during the prosecution of U.S. Appl. No. 15/740,365.
European Search Report dated Jun. 21, 2019 which issued during the prosecution of European Application No. 16817348.2.
An International Search Report and a Written Opinion both dated Aug. 5, 2018, which issued during the prosecution of Applicant's PCT/IL2018/050409.
U.S. Appl. No. 62/813,292, filed Mar. 4, 2019.
European Search Report dated Jun. 4, 2020, which issued during the prosecution of Applicant's European App No. 20160966.6.
An Office Action dated Jun. 22, 2020, which issued during the prosecution of U.S. Appl. No. 15/740,365.
An International Search Report and a Written Opinion both dated Jun. 9, 2020, which issued during the prosecution of Applicant's PCT/IL2020/050246.
An International Search Report and a Written Opinion both dated May 15, 2020, which issued during the prosecution of Applicant's PCT/IL2020/050249.
U.S. Appl. No. 62/629,038, filed Feb. 11, 2018.
European Search Report dated May 12, 2021 which issued during the prosecution of Applicant's European App No. 20212979.7.
European Search Report dated Oct. 8, 2021 which issued during the prosecution of Applicant's European App No. 18905766.4., 8pp.
Notice of Allowance dated Aug. 4, 2021, which issued during the prosecution of U.S. Appl. No. 16/808,652, 79pp.

* cited by examiner

FLEX-STROKE INFUSION PUMP

CROSS REFERENCE TO RELATED APPLICATIONS

This application is a National Phase of PCT Patent Application No. PCT/IL2018/050409 having International filing date of Apr. 9, 2018, which claims the benefit of priority of U.S. Provisional Application No. 62/629,038 filed on Feb. 11, 2018. The contents of the above applications are all incorporated by reference as if fully set forth herein in their entirety.

FIELD OF THE INVENTION

The present invention relates generally to the field of medical devices for providing fluid to a patient. More specifically, the present invention relates to infusion pumps configured to prevent or compensate for degradation of infusion tubes operationally connected to the pump.

BACKGROUND

Infusion pumps are configured to administer fluid to a patient via a conduit such as an infusion tube or a cassette at high accuracy and often for a prolonged period of time. Infusion tubes are accommodated in the infusion pump in such manner that a plunger can squeeze the surface of the infusion tube, thereby causing delivery of the infusion fluid.

Infusion pumps administer fluids in ways that would be impractical and expensive/unreliable if performed manually by nursing staff. For example, an infusion pump assembly may repeatedly administer small quantities of an infusible fluid (e.g., 0.1 mL per hour). However, common disposable infusion tubes are prone to deform or rupture when being continuously compressed, consequently affecting the precision of the delivery.

SUMMARY OF THE INVENTION

The hereindisclosed infusion pump advantageously includes a controller configured to control the position of a plunger in such manner that an infusion tube connected to the infusion pump remains partially squeezed dozing essentially the entire operation of the pump.

That is, in its upper position (also referred to herein as an upper squeezing position) the plunger mildly squeezes the infusion tube, such that opposite sides of an inner surface of the infusion tube do not contact each other. This is as opposed to common infusion pumps, which in their upper position (also referred to herein as an uppermost position) do not squeeze the infusion tube; in fact, the plunger is typically elevated to a position in which it does not touch the infusion tube's outer surface.

As used herein, the term "mildly squeezing" refers to the plunger pressing upon the infusion tube sufficiently to cause a change in the shape of the infusion tube's inner lumen, as compared to a hilly relaxed tube. According to some embodiments, at its upper squeezing position, when mildly squeezed, the infusion tube is more than 0% and less than 10% squeezed, as compared to a hilly squeezed infusion tube. According to some embodiments, at its upper squeezing position, when mildly squeezed, the infusion tube is more than 5% and less than 10% squeezed, as compared to a hilly squeezed infusion tube.

In the plunger's lower position (also referred to herein as a lower squeezing position), the squeezing of the infusion tube is increased, yet still the opposite sides of the inner surface of the infusion tube do not contact each other. Again, this is different than common infusion pumps, which typically are configured to squeeze the infusion tube to a maximum (also referred to herein as a lowermost position), i.e. such that the opposite sides of the inner surface of the infusion tube become basically aligned. According to some embodiments, in its lower squeezing position, the infusion tube is less than 100% squeezed and more than 80% squeezed, as compared to a fully squeezed infusion tube. According to some embodiments, in its lower squeezing position, the infusion tube is less than 95% squeezed and more than 80% squeezed, as compared to a fully squeezed infusion tube.

Advantageously switching between intermediate rather than extreme positions ensures accurate delivery even during prolonged delivery.

Complete squeezing of the infusion tube causes bottoming out and high stress to the tubing walls, which in turn leads to continuous degradation and impaired accuracy over time. This is particularly a problem when utilizing DEHP-free PVC, since PVC is an overdamped spring that does not truly hollow the plunger, as opposed to, for example, silicon tubes. Utilizing a less severe lower position advantageously prevents such degradation.

In addition, due to the plunger executing a mild squeeze even in the upper position (deeper upper position of the plunger), the tube follows the plunger to the upper position and the springiness of the tubing is thus maintained throughout the pumping cycle. As a result, the need for incorporating complicated algorithms in an attempt to compensate for changes in flow rate over time is obviated. In fact, the flow rate stability of the hereindisclosed infusion pump is far superior to that of infusion pumps utilizing flow rate compensation algorithms as further demonstrated hereinbelow.

According to some embodiments, the infusion pump, disclosed herein, is further configured to determine a wait period during which the plunger "waits" in its (deep) upper position, prior to the opening of the infusion pump's downstream valve. This allows the infusion tube to fully engage the plunger prior to the opening of the downstream valve, and thus increases accuracy, as the volume of the tube is constant. In addition, an ascending of the infusion tube whilst the downstream valve is open, causing liquids to be extracted from the patient, is beneficially prevented.

According to some embodiments, during the intake phase (suction of liquid from an IV bag or syringe), the plunger can be raised to a position above the upper position and then descended back to the upper position, mildly squeezing the infusion tube. This does not only allow more room for relaxation of the infusion tube, but also enables pumping a small bolus into the syringe, thus reducing the vacuum that is created during the intake.

Advantageously the controller may be configured to calibrate and/or optimize the upper and lower squeezing positions of the plunger, thus facilitating operation with infusion tubes of different dimensions and consistencies.

According to some embodiments, there is provided an infusion pump comprising a plunger; a proximal valve located proximally to said plunger; a distal valve located distally to said plunger; and a controller configured to control infusion fluid delivery to the subject and infusion fluid intake from a reservoir (also referred to as an infusion source). The controlling of the intake of fluid comprises: closing of said distal valve, opening of said proximal valve, moving of said plunger to an upper squeezing position, in which upper squeezing position of said plunger is configured to partially squeeze an infusion tube, while facilitating intake of fluid; and determining a "wait" period, following the intake, during which wait period said plunger remains at said upper squeezing position, thereby ensuring full recovery of the tube to engagement of the infusion tube with the plunger. The controlling delivery comprises: closing of said proximal valve and opening of said distal valve, while said plunger is at the upper squeezing position, descending of said plunger from the upper squeezing position to a lower squeezing position, wherein at both the upper squeezing position and the lower squeezing position, said plunger is configured to squeeze a section of an infusion tube, such that opposite sides of an inner surface of said section do not contact one another, thereby facilitating delivery of an essentially constant volume of infusion fluid to the subject regardless of a potential degradation of the infusion tube.

According to some embodiments, the plunger is configured to contact an outer surface of the infusion tube from the end of intake to end of delivery operation thereof.

According to some embodiments, at the lower squeezing position, the plunger is configured to squeeze the section of the infusion tube to form a first inner tube cross section and wherein, at the upper squeezing position, the plunger is configured to squeeze the section of the infusion tube to form a second inner tube cross section, wherein the second inner tube cross section is larger than the first inner tube cross section and smaller than a cross section of the infusion tube, when not-squeezed.

According to some embodiments, the infusion pump further comprises a motor in communication with the controller, the motor configured to operate the plunger. According to some embodiments, the motor is further configured to operate the proximal valve, the distal valve or both. Additionally or alternatively, the infusion pump further comprises a second motor configured to operate the proximal valve, the distal valve or both.

According to some embodiments, the infusion tube is a DEHP-free PVC infusion tube.

According to some embodiments, the controller is configured to calibrate the upper squeezing position and the lower squeezing position of the plunger according to dimensions of the infusion tube.

According to some embodiments, controlling the intake of infusion fluid further comprises initially positioning of the plunger to a position above the upper squeezing position followed by a descending of the plunger to the upper squeezing position, while the proximal valve is open, thereby allowing residual fluid to backflow towards the reservoir.

According to some embodiments, the wait period has a maximum duration based on and/or defined by the flow continuity and flow rate.

According to some embodiments, there is provided an infusion pump comprising: a plunger; a proximal valve located proximally to the plunger; a distal valve located distally to the plunger; and a controller configured to control an infusion fluid delivery to the subject and an infusion fluid intake from a reservoir. Controlling the intake of fluid comprises: closing of said distal valve, opening of said proximal valve, moving of the plunger from the lower position to the upper position and above an upper squeezing position; and descending of the plunger to the upper squeezing position, in which upper squeezing position the plunger is configured to partially squeeze an infusion tube, while allowing intake of infusion fluid. Controlling the intake of infusion fluid further comprises determining a "wait" period, following the intake, during which wait period the plunger remains at the upper squeezing position or above it, thereby ensuring engagement of the infusion tube with the plunger.

According to some embodiments, controlling the delivery of the infusion fluid comprises: closing of the proximal valve and opening of the distal valve, while the plunger is at the upper squeezing position, descending of the plunger from the upper squeezing position to a lower squeezing position, wherein at both the upper squeezing position and the lower squeezing position, the plunger is configured to squeeze a section of an infusion tube, such that opposite sides of an inner surface of the section do not contact one another, thereby facilitating delivery of an essentially constant volume of infusion fluid to the subject regardless of a potential degradation of the infusion tube.

According to some embodiments, the plunger is configured to contact an outer surface of the infusion tube section during the entire delivery thereof.

According to some embodiments, the infusion pump further comprises a motor in communication with the controller, the motor configured to operate said plunger. According to some embodiments, the motor is further configured to operate the proximal valve, the distal valve or both. Additionally or alternatively, the infusion pump further comprises a second motor configured to operate the proximal valve, the distal valve or both.

According to some embodiments, the infusion tube is a DEHP-free PVC infusion tube.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1A:
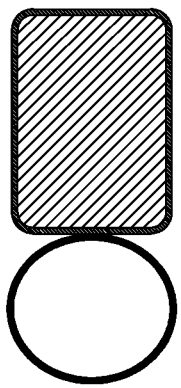
FIG. 1A schematically illustrates upper and lower positions of prior art plungers.
Figure 1A:
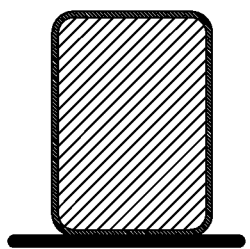

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided an infusion pump including a plunger; a proximal valve located proximally to the plunger; a distal valve located distally to the plunger; and a controller configured to control an infusion fluid delivery to the subject, wherein controlling delivery comprises triggering closing of the proximal valve, while the plunger is at an upper squeezing position, and triggering descending of the plunger from the upper squeezing position to a lower squeezing position, wherein at both the upper squeezing position and the lower squeezing position, said plunger is configured to squeeze a section of an infusion tube, such that opposite sides of an inner surface of said section do not contact one another, thereby facilitating delivery of an essentially constant volume of infusion fluid to the subject regardless of a potential degradation of the infusion tube.

As used herein, the term "upper squeezing position" refers to a position of a plunger at which an infusion tube is mildly squeezed (i.e. higher than a position at which the tube is not squeezed), without having the opposite sides of an inner surface of the squeezed section contacting one another. According to some embodiments, the delivery phase of the infusion pump is initiated at "upper squeezing position".

As used herein, the term "lower squeezing position" refers to a position of the plunger at which an infusion tube is squeezed to a larger extent as compared to the upper squeezing position, yet still without having the opposite sides of an inner surface of the squeezed section contacting one another. According to some embodiments, the delivery phase of the infusion pump is initiated at "upper squeezing position".

As used herein, the term "degradation" may refer to the tube losing its springiness, becoming deformed, bottoming out, or otherwise changing its shape or consistency in a manner affecting the drug delivery accuracy. According to some embodiments, the infusion tube may be a DEHP-free PVC infusion tube, a DEHP containing infusion tube, a polyethylene (PE) tube, a silicone tube, or the like. Each possibility is a separate embodiment.

As used herein, the term "infusion fluid" may refer to any fluid delivered to the patient such as, but not limited to, insulin, nutrients, saline solution, antibiotics, analgesics, anesthetics, hormones, vasoactive drugs, and chelation drugs, and any other therapeutic fluids or combination of fluids.

According to some embodiments, the plunger is configured to contact an outer surface of the infusion tube section during essentially the entire operation of the infusion pump. According to some embodiments, the plunger is configured to contact an outer surface of the infusion tube section during essentially the entire phase of delivery of the infusion fluid to the subject. According to some embodiments, the plunger is configured to some extent squeeze the infusion tube section, without having the opposite sides of an inner surface of the squeezed section contacting one another, during essentially the entire operation of the infusion pump. According to some embodiments, the plunger is configured to some extent squeeze the infusion tube section, without having the opposite sides of an inner surface of the squeezed section contacting one another, during essentially the entire phase of delivery of the infusion fluid to the subject. According to some embodiments, the plunger does not facilitate full relaxation of the infusion tube at any point of operation. According to some embodiments, the plunger does not fully squeeze/press the infusion tube at any point of operation.

As used herein, the term "entire" may refer to at least, at least 95% or at least 98% of the operation of the infusion pump/of the delivery phase. It is thus understood that briefly elevating the plunger during operation may be within the scope of this disclosure.

As used herein, the term "to some extent" with referral to the squeezing of the infusion tube refers to a squeezing of the infusion tube rendering the cross section of the squeezed section's lumen smaller than that of the infusion tube when non-squeezed, without having the opposite sides of an inner surface of the squeezed section contacting one another.

According to some embodiments, at the upper squeezing position, the plunger is configured to squeeze the section of the infusion tube to form a first inner tube cross section and wherein at the lower squeezing position, the plunger is configured to squeeze the section of the infusion tube to form a second inner tube cross section, wherein the second inner tube cross section is smaller than the first inner tube cross section and larger than a cross section of the infusion tube when non-squeezed.

According to some embodiments, the inner tube cross section of the infusion tube when the plunger is in its upper position is 50%-90% the size of the inner tube cross section of the infusion tube when non-squeezed. Each possibility is a separate embodiment.

According to some embodiments, the inner tube cross section of the infusion tube when the plunger is in its lower position is between 50%-10%, larger than the size of the inner tube cross section. Each possibility is a separate embodiment.

Any combination of upper and lower squeezed positions is a specific embodiment.

According to some embodiments, for a typical tube of 3 mm inner diameter and a wall thickness of 0.5 mm, a typical upper squeezing position, of the plunger is positioned about 0.8 mm to 1.8 mm, lower than the diameter of a non-squeezed tube. Each possibility is a separate embodiment.

According to some embodiments, for the same tube defined above, the lower squeezing position of the plunger is positioned about 2.0 mm-2.8 mm, below the non-squeezed tube. Each possibility is a separate embodiment.

According to some embodiments, the infusion pump is configured to maintain an essentially constant flow rate during the entire delivery of an infusion fluid. As used herein, the term "essentially constant" refers to a flow rate changing by less than 2% during the entire delivery. As a non-limiting example, the infusion pump is configured to maintain a delivery of an infusion fluid at a flow rate of 1 mL/hour±0.01 mL for at least 20, at least 36 or at least 96 hours.

According to some embodiments, the controller is further configured to control the intake of an infusion fluid from a reservoir, such as, but not limited to, an IV-bag or a syringe. According to some embodiments, controlling the intake of the infusion fluid comprises triggering opening of the proximal valve, closing of the distal valve and elevating the plunger to the upper squeezing position. According to some embodiments, during the intake phase, the plunger may initially be elevated to a position above the upper squeezing position for a brief moment (e.g. 1 sec or less) and then lowered back to the upper squeezing position. This may advantageously allow more room for the infusion tube to assume a relaxed configuration. In addition, when using a syringe as the reservoir, the initial elevation of the plunger to a position above the upper squeezing position prior to assuming the upper squeezing position may pump a small bolus into the syringe, thus reducing the residual vacuum left in the syringe at the end of the intake.

According to some embodiments, the pump further includes a motor in communication with the controller, the motor configured to operate the plunger. According to some embodiments, the motor may further be configured to operate the proximal valve, the distal valve or both. Alternatively, the pump may include one or two additional motors configured to operate the proximal valve, the distal valve or both. According to some embodiments, the controller may control the operation of the motor, thereby determining the exact position of the plunger. This may advantageously allow calibrating the upper and lower squeezing positions vis-à-vis the floor against which the infusion tube is squeezed according to dimensions and/or consistency of the infusion tube.

According to some embodiments, the controller may further be configured to determine a "wait" period, during which wait period the plunger remains at the upper squeezing position, thereby ensuring full engagement of the infusion tube with the plunger, prior to the opening of the infusion pump's downstream valve. This advantageously increases the accuracy of infusion fluid delivery in that the volume delivered remains constant even if the infusion tube has undergone degradation. Furthermore, due to the infusion tube fully engaging the plunger, a persistent ascending of the infusion tube after opening of the downstream valve is essentially prevented. Extraction of liquids from the patient is prevented. The length of the wait depends on the flow continuity requirements and the flow rate. For low flow rates (1-10 mL/hr) and flow continuity of bolus every 20 sec, the wait can last up to 18 sec. For high flow rates, the wait time is shorter (e.g. about 10 sec) and for very high flow rates (999 mL/hr) it may last less than 1 second. The long wait is particularly advantageous for low flow rates where the tube squeeze duty cycle is very long.

According to some embodiments, the wait period may be at least two seconds, or at least 5 seconds. According to some embodiments, the duration of the wait is dependent on the flow rate of the infusion fluid and/or the length of the plunger.

According to some embodiments, there is provided a method of operation of an infusion pump, the method comprising;

providing/utilizing an infusion pump comprising a plunger; a proximal valve located proximally to the plunger and a distal valve located distally to the plunger;

triggering opening of the proximal valve, triggering closing of the distal valve; and triggering the positioning of the plunger to an upper squeezing position at which the infusion tube positioned within the infusion pump is mildly squeezed yet without having opposite sides of the inner surface of its squeezed section contacting one another, thereby causing intake of fluid from a reservoir;

positioning/holding the plunger in the upper squeezing position;

triggering closing of the proximal valve, while the plunger is at the upper squeezing position; and triggering descending of the plunger from the upper squeezing position to a lower squeezing position, at which the infusion tube is further squeezed, yet still without having opposite sides of the inner surface of its squeezed section contacting one another, thereby facilitating delivery of an essentially constant volume of the infusion fluid to a subject, regardless of a potential degradation of the infusion tube.

According to some embodiments, the infusion tube is at no point of operation fully squeezed/pressed by the plunger.

According to some embodiments, the method may further include briefly elevating the plunger to a position above the upper squeezing position, (while the proximal valve is open, and the distal valve closed) prior to the positioning of the plunger at the upper squeezing position, thereby allowing a small bolus of infusion fluid to flow into the syringe, thus reducing the vacuum created therein during the intake, as well as allowing more room for the infusion tube to assume a relaxed configuration.

According to some embodiments, the method may further include determining a "wait" period configured to ensure full engagement of the infusion tube with the plunger, wherein during the wait period the plunger remains at the upper squeezing position, prior to the opening of the infusion pump's downstream valve.

Reference is now made to FIG. 1A, which schematically illustrates upper and lower positions of prior art plungers. As shown in the figure, typical plungers are configured to assume an upper position (also referred to herein as an uppermost position) at which the infusion tube is fully relaxed (during fluid intake) and a lower position (also referred to herein as a lowermost position) at which the infusion tube is fully squeezed (during infusion fluid delivery).

Figure 1B:
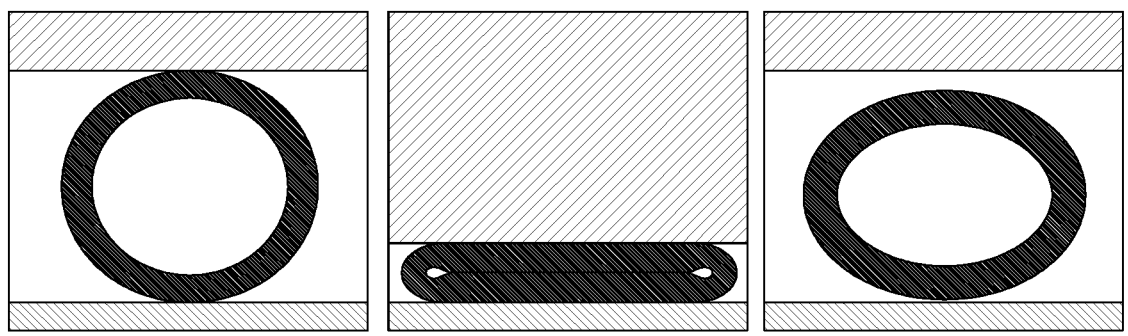
FIG. 1B shows exemplary photos of a DEHP-free PVC infusion tube prior to use (left panel), and during use with a prior art plunger at its lower position (center panel) and its upper position (right panel)

As evident from FIG. 1B which shows exemplary photos of a DEHP-free PVC infusion tube prior to use (left panel), during use at its lower position (center panel) and during use at its upper position (center panel); during use the infusion tube undergoes degradation, i.e. loses its springiness and/or shape. That is, when the plunger fully squeezes the infusion tube, high stress is incurred, and the tube tends to bottom out. With time, when the plunger is elevated to its uppermost position (during intake), the tube acts as an overdamped spring and fails to fully engage the plunger. This, on the one hand, results in a lower volume of intake and thus to inaccurate/insufficient infusion fluid delivery, which at times may be harmful and even hazardous to the patient's health. To solve this problem, prior art pumps have been provided which include complex algorithms compensating for the changes in flow rate. However, as further demonstrated hereinbelow, such algorithms fail to accurately predict the changes in flow rate and variations therein are still prevalent. In addition, a continuous ascending of the tube towards the plunger may occur after the downstream valve has been opened, thus causing liquids to be extracted from the patient.

Figure 2A:
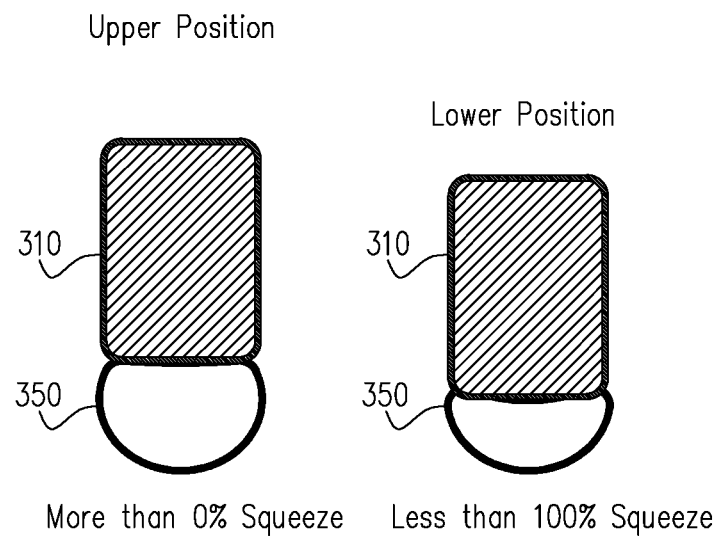
FIG. 2A schematically illustrates upper and lower positions of the hereindisclosed plunger; according to some embodiments.

Reference is now made to FIG. 2A, which schematically illustrates upper and lower positions of the hereindisclosed plungers. As shown in the figure, the hereindisclosed plunger is configured to assume an upper position (also referred to herein as an upper squeezing position) at which the infusion tube is mildly squeezed (during fluid intake) and a lower position (also referred to herein as a lower squeezing position) at which the infusion tube is squeezed to a larger extent than at the upper squeezing position yet without having opposite sides of the tube's inner surface contacting each other (during infusion fluid delivery).

Figure 2B:
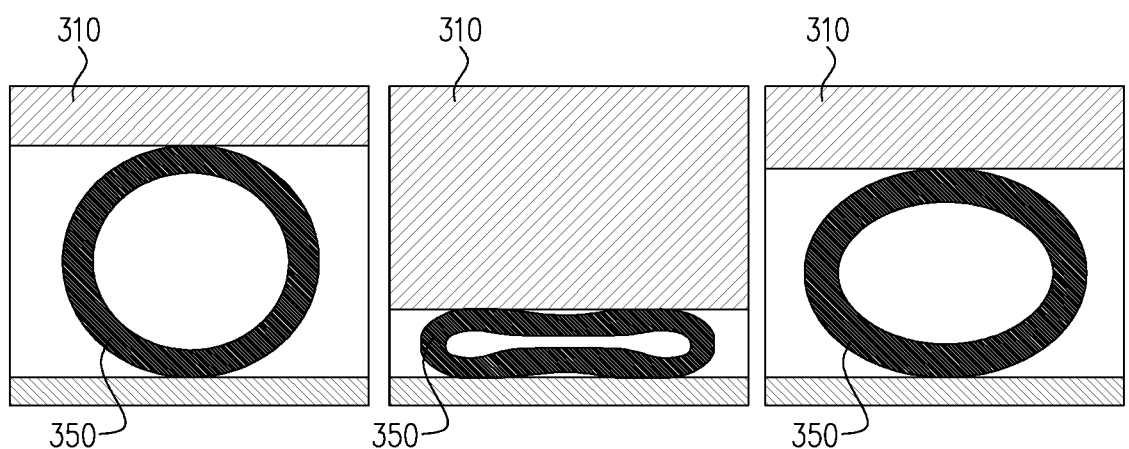
FIG. 2B shows exemplary photos of a DEHP-free PVC infusion tube prior to use (left panel), and during use with the hereindisclosed plunger at its lower position (center panel) and its upper position (right panel)

Advantageously and as evident from FIG. 2B which shows exemplary photos of a DEHP-free PVC infusion tube prior to use (left panel), and during use with the hereindisclosed plunger at its lower position (center panel), and its upper position (right panel); a crushing of the tube's wall is avoided, and the springiness of the tube is much less affected. That is, at the lower squeezing position, much less stress is incurred on the tubing, and the bottoming out obtained when fully squeezing the tube is essentially non-existent. In addition, due to the fact that the plunger squeezing the tube even at its upper squeezing position ensures that the tube engages the plunger at all times. As a result, the delivery flow rate remains constant during the entire use, and the need for compensating algorithms is obviated. In addition, since full engagement of the tube with the plunger is ensured, the continuous ascending of the tube towards the plunger, after opening of the downstream valve, is largely prevented. Altering between two squeezed states strengthens the minimum strength of the tube spring in the upper position and reduces the maximum tube squeeze at the lower position to reduce the degradation.

Figure 3:
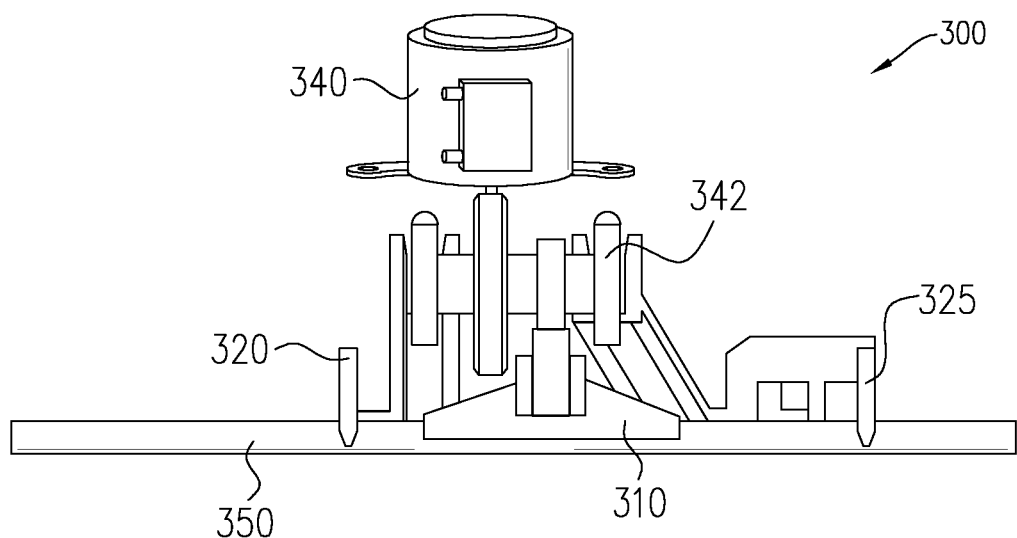
FIG. 3 schematically illustrates an infusion pump with a plunger having intermediate squeezing positions, according to some embodiments.

Reference is now made to FIG. 3 which schematically illustrates an infusion pump 300 with a plunger 310 having intermediate squeezing positions, according to some embodiments. Infusion pump 300 includes a proximal valve 320, also referred to herein as an inlet valve, positioned proximally/upstream to plunger 310 and configured to allow flow of infusion fluid from a reservoir (not shown) to an infusion tube 350. Infusion pump 300 further includes a distal valve 325, also referred to herein as an outlet valve, positioned distally/downstream to plunger 310 and configured to allow flow of infusion fluid from infusion tube 350 to a patient (not shown). The positioning of plunger 310, proximal valve 320 and distal valve 325 are carried out by motor 340 and associated cam shaft 342, although other embodiments, according to which positioning of plunger 310, proximal valve 320 and distal valve 325 is executed by separate motors, are also possible and within the scope of this disclosure. During intake of infusion fluid from a reservoir, a controller (not shown) is configured to control operation of motor 340 and associated cam shaft 342, which in turn brings about opening of proximal valve 320, closing of the distal valve 325, and positioning of plunger 310 in an upper squeezing position, at which infusion tube 350, positioned within infusion pump 300, is mildly squeezed, yet allowing infusion fluid intake. During delivery of infusion fluid, the controller triggers motor 340 and associated cam shaft 342 to close proximal valve 320, while plunger 310 is in its upper squeezing position; to open distal valve 325 and descending plunger 310 from the upper squeezing position to a lower squeezing position, at which the infusion tube is further squeezed, yet without having opposite sides of the inner surface of its squeezed section contacting one another, thereby facilitating delivery of an essentially constant volume of infusion fluid to the patient.

According to some embodiments, the controller may further be configured to define a "wait" period configured to ensure full engagement of infusion tube 350 with the plunger 310, wherein, during the wait period, plunger 310 remains at the upper squeezing position, while distal valve 325 is open. As a non-limiting example, if the maximum no flow time is set to 20 seconds and the closing of the distal and opening of the proximal valves takes 3 seconds, the controller may be configured to retain plunger 310 at the upper squeezing position for an additional 17 seconds, prior to commencing delivery by lowering plunger 310 to the lower squeezing position after the valves are switched back to delivery position. The wait period ensures full engagement of infusion tube 350 with plunger 310 prior to infusion fluid delivery and thus guarantees that an exact and constant amount of infusion fluid is delivered to the patient. In addition, by preventing continuous ascending/relaxing of infusion tube 350 during delivery (which may occur if full engagement between infusion tube 350 and plunger 310 is not achieved), liquid may be sucked from the patient into infusion tube 350. This may in turn result in blood entering the catheter and the tube, and cause occlusions in the infusion tube. In addition, the blood in the tube is also often found visually unpleasant to the patient and his/her surroundings. Defining a wait period may be of particular importance for low flow rate delivery in which case infusion tube 350 is squeezed by plunger 310 (in its lower squeezing position) for a prolonged period of time (e.g. 1-3 hours depending on the plunger length, tube ID and flow rate). The intake of the infusion fluid has a short duration (a few seconds) and, without the wait, will not be sufficient to recover the tube to the original upper position of the plunger, hence, will reduce the intake volume.

According to some embodiments, the controller may be further configured to trigger an elevating of plunger 310 to a position above the upper squeezing position (but still somewhat squeezed), while proximal valve 320 is open, and distal valve 325 closed, such that lowering of plunger 310 to the upper squeezing position causes a small bolus of infusion fluid to flow into the reservoir. Such initial backflow may be particularly advantageous when the infusion source is a syringe, in that it enables reducing the residual vacuum created within the syringe.

Figure 4:
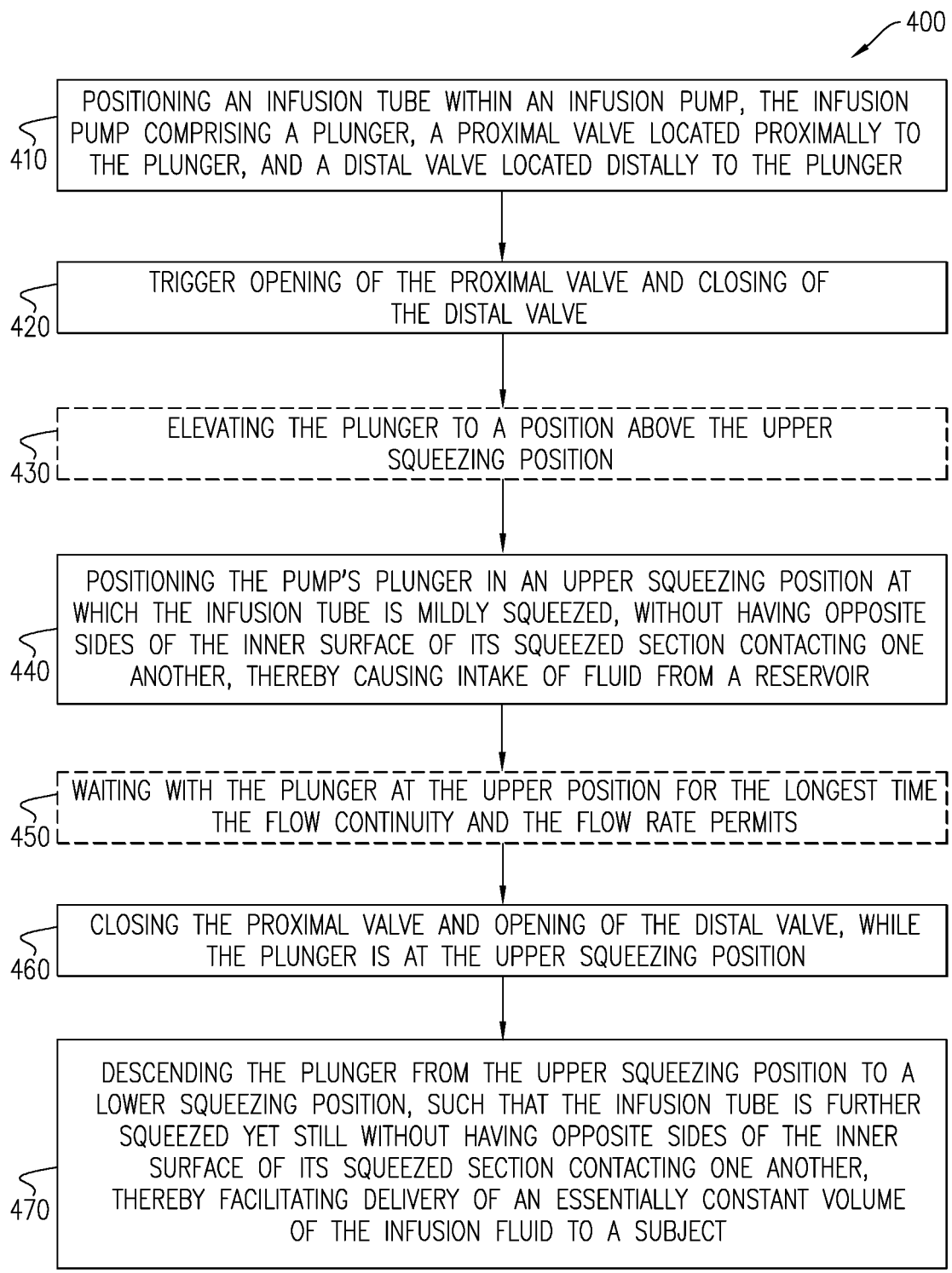
FIG. 4 is an illustrative flowchart for operating an infusion pump, according to some embodiments.

Reference is now made to FIG. 4 which is an illustrative flowchart 400 for operating an infusion pump, according to some embodiments.

Steps 410 to 450 are steps associated with intake of infusion fluid from a reservoir (also referred to herein as infusion source).

In step 410 an infusion tube is positioned within an infusion pump comprising a plunger, a proximal valve located proximally to the plunger, and a distal valve located distally to the plunger.

In step 420 an opening of the proximal valve and a closing of the distal valve is triggered, followed by a positioning of the plunger in an upper squeezing position at which the infusion tube is mildly squeezed (step 440), yet without having opposite sides of the inner surface of its squeezed section contacting one another, thereby causing intake of fluid from a reservoir.

Optionally, prior to positioning the plunger in its upper squeezing position, the method may include a step 430 in which the plunger is, for most of the wait time, elevated to a position above the upper squeezing position, (while the proximal valve is open, and the distal valve closed). This step may be particularly advantageous when the reservoir is a syringe in that it allows a small bolus of infusion fluid to flow into the syringe, thus reducing the residual vacuum created therein during the intake.

Optionally, after intake of infusion fluid from the reservoir is completed, the method may further include a step 450 at which the plunger "waits" at the upper squeezing position for the longest time the flow continuity and the flow rate permits, so as to ensure full engagement of the infusion tube with the plunger. According to some embodiments, the length of the wait period may depend on the length of the intake and may, for example, range between 2 seconds and 18 seconds when the required flow continuity is to have a maximum delivery every 20 seconds. If the flow continuity is defined by 10 minutes of maximum no flow time, the wait can last 10 minutes minus a few seconds. The choice of wait is the longest possible under the specific flow continuity and flow rate requirements.

Steps 460 to 470 are steps associated with delivery of the infusion fluid to a patient.

In step 460 the plunger is held in the upper squeezing position while closing of the proximal valve and opening of the distal valve is triggered. Subsequently, in step 470, a descending of the plunger from the upper squeezing position to a lower squeezing position is triggered, thereby causing the infusion tube to be further squeezed yet still without having opposite sides of the inner surface of its squeezed section contacting one another. As a result, delivery of an essentially constant volume of the infusion fluid to a subject is facilitated, regardless of a potential degradation of the infusion tube.

EXAMPLES

Example 1—Flow Rate Stability

In order to evaluate the flow rate stability of the hereindisclosed infusion pump a comparative study was set up. The study evaluated the flow rate over time of an infusion fluid delivered by the hereindisclosed infusion pump (Avoset) as compared to that obtained using a known infusion pump including a compensation algorithm configured to mathematically compensate for changes in flow rate caused by tube degradation.

Figure 5A:
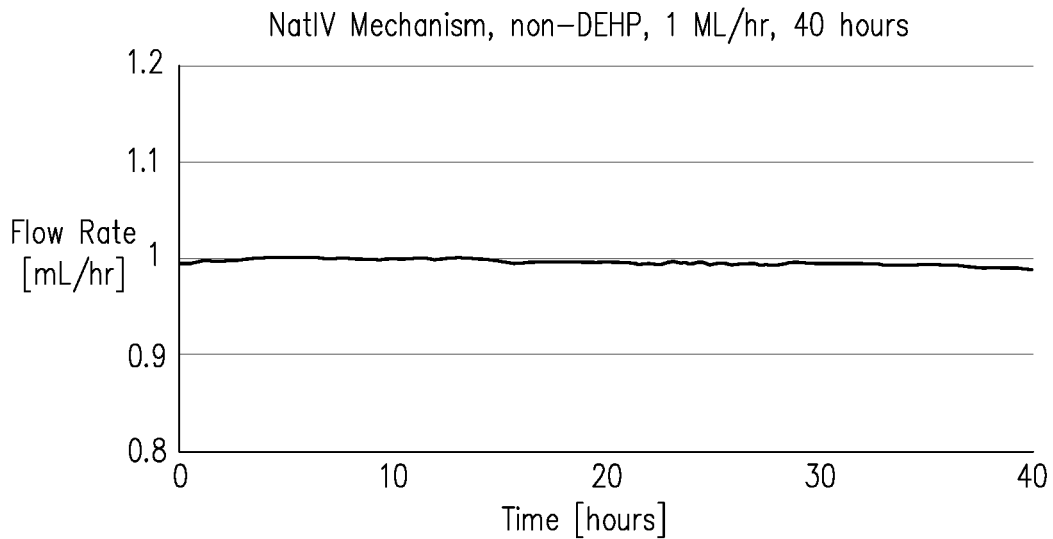
FIG. 5A shows the flow rate over time obtained using the hereindisclosed infusion pump (NatIV)
Figure 5B:
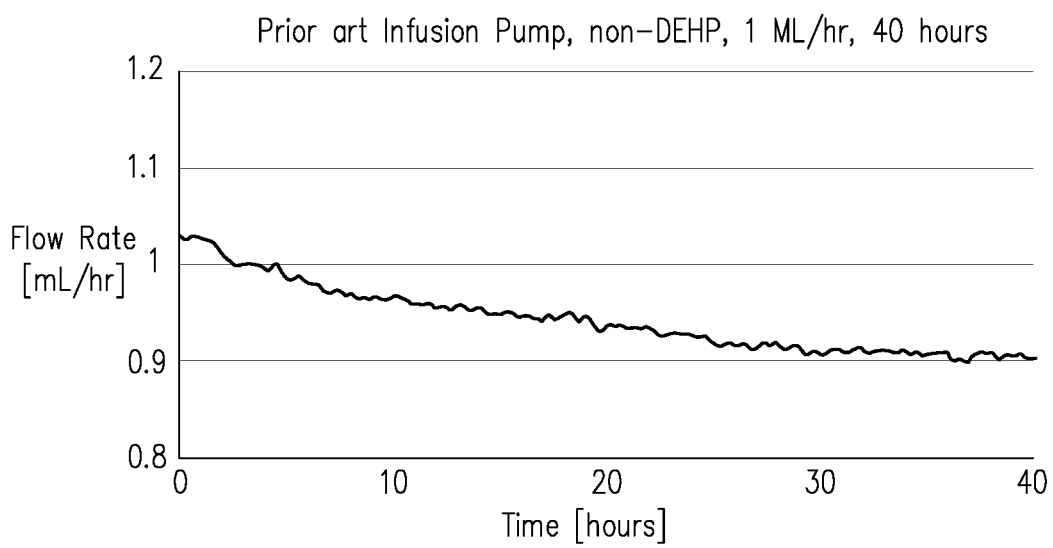
FIG. 5B shows the flow rate over time obtained using a prior art infusion pump including compensation algorithm.

As seen from FIG. 5A, when utilizing the hereindisclosed infusion pump for delivery of an infusion fluid at a flow rate of 1 mL/hr, 40 hours, a constant 1 mL/hr flow rate is obtained during the entire course of the delivery. This, as opposed to a prior art infusion pump, which despite incorporating compensation algorithms, has a declined flow rate over time, such that 30 hr after commencing the delivery, a flow rate of 0.9 mL/hr instead of 1 mL/hr is obtained, as seen in FIG. 5B.

This result clearly emphasizes the unexpected and convincing advantage of the hereindisclosed infusion pump, which is capable of ensuring a constant delivery of infusion fluid for 40 hours and more.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but not limited to, any type of read-only memories (ROMs), random access memories (RAMs), electrically programmable read-only memories (EPROMs), electrically erasable and programmable read only memories (EEPROMs), or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What we claim is:

1. An infusion pump comprising:
    a plunger;
    a proximal valve located proximally to said plunger;
    a distal valve located distally to said plunger; and
    a controller configured to control an infusion fluid delivery to a subject and an infusion fluid intake from a reservoir,
        wherein controlling the infusion fluid intake comprises:

closing said distal valve,
opening said proximal valve,
moving said plunger to an upper squeezing position, in which said plunger is configured to partially squeeze an infusion tube disposed within the infusion pump to facilitate intake of fluid into the infusion tube; and
providing a wait period, following the infusion fluid intake, during which said plunger remains at said upper squeezing position, thereby providing time for recovery of the infusion tube such that the infusion tube engages with the plunger;
wherein controlling the infusion fluid delivery comprises:
closing said proximal valve and opening said distal valve, while said plunger is at the upper squeezing position, and
lowering said plunger from the upper squeezing position to a lower squeezing position,
wherein at both the upper squeezing position and the lower squeezing position, said plunger is configured to squeeze a section of the infusion tube, such that opposite sides of an inner surface of said section do not contact one another, and
wherein the controller is configured to set a duration of the wait period as a function of a maximum no-flow time between the infusion fluid intake and the infusion fluid delivery.

2. The infusion pump of claim 1, wherein said plunger is configured to contact an outer surface of the infusion tube from an end of infusion fluid intake to an end of the infusion fluid delivery.

3. The infusion pump of claim 1, wherein at the lower squeezing position said plunger is configured to squeeze the section of the infusion tube to form a first inner tube cross section, and wherein at the upper squeezing position said plunger is configured to squeeze the section of the infusion tube to form a second inner tube cross section, wherein the second inner tube cross section is larger than the first inner tube cross section and smaller than a cross section of the infusion tube when not squeezed.

4. The infusion pump of claim 1, further comprising a motor in communication with said controller, said motor configured to operate said plunger.

5. The infusion pump of claim 4, wherein said motor is further configured to operate said proximal valve, said distal valve, or both.

6. The infusion pump of claim 4, wherein the motor is a first motor and the infusion pump further comprises a second motor configured to operate said proximal valve, said distal valve, or both.

7. The infusion pump of claim 1, wherein said infusion tube is a DEHP-free PVC infusion tube.

8. The infusion pump of claim 1, wherein the controller is configured to calibrate the upper squeezing position and the lower squeezing position of the plunger according to dimensions of the infusion tube.

9. The infusion pump of claim 1, wherein controlling the infusion fluid intake further comprises initially positioning the plunger in a position that is above the upper squeezing position, followed by lowering the plunger to the upper squeezing position while the proximal valve is open so as to allow residual infusion fluid to backflow towards the reservoir.

10. An infusion pump comprising:
a plunger;
a proximal valve located proximally to said plunger;
a distal valve located distally to said plunger; and
a controller configured to control an infusion fluid delivery to a subject and an infusion fluid intake from a reservoir,
wherein controlling the infusion fluid intake comprises:
closing said distal valve,
opening said proximal valve,
moving said plunger to an upper squeezing position, in which said plunger is configured to partially squeeze an infusion tube disposed within the infusion pump to facilitate intake of fluid into the infusion tube; and
providing a wait period, following the infusion fluid intake, during which said plunger remains at said upper squeezing position, thereby providing time for recovery of the infusion tube such that the infusion tube engages with the plunger;
wherein controlling the infusion fluid delivery comprises:
closing said proximal valve and opening said distal valve, while said plunger is at the upper squeezing position, and
lowering said plunger from the upper squeezing position to a lower squeezing position,
wherein at both the upper squeezing position and the lower squeezing position, said plunger is configured to squeeze a section of the infusion tube, such that opposite sides of an inner surface of said section do not contact one another, and
wherein the controller is configured to set a duration of the wait period as a function of flow rate of the infusion fluid delivery to the subject.

11. The infusion pump of claim 10, wherein said plunger is configured to contact an outer surface of the infusion tube from an end of infusion fluid intake to an end of the infusion fluid delivery.

12. The infusion pump of claim 10, wherein at the lower squeezing position said plunger is configured to squeeze the section of the infusion tube to form a first inner tube cross section, and wherein at the upper squeezing position said plunger is configured to squeeze the section of the infusion tube to form a second inner tube cross section, wherein the second inner tube cross section is larger than the first inner tube cross section and smaller than a cross section of the infusion tube when not squeezed.

13. The infusion pump of claim 10, further comprising a motor in communication with said controller, said motor configured to operate said plunger.

14. The infusion pump of claim 13, wherein said motor is further configured to operate said proximal valve, said distal valve, or both.

15. The infusion pump of claim 13, wherein the motor is a first motor and the infusion pump further comprises a second motor configured to operate said proximal valve, said distal valve, or both.

16. The infusion pump of claim 10, wherein said infusion tube is a DEHP-free PVC infusion tube.

17. The infusion pump of claim 10, wherein the controller is configured to calibrate the upper squeezing position and the lower squeezing position of the plunger according to dimensions of the infusion tube.

18. The infusion pump of claim 10, wherein the control is configured to control the infusion fluid intake by initially positioning the plunger in a position that is above the upper squeezing position, followed by lowering the plunger to the upper squeezing position while the proximal valve is open so as to allow residual infusion fluid to backflow towards the reservoir.

19. The infusion pump of claim 10, wherein the controller is configured to set the duration of the wait period as a function of flow rate of the infusion fluid delivery to the subject by setting the duration of the wait period as a function of a maximum no-flow time between the infusion fluid intake and the infusion fluid delivery.

* * * * *